United States Patent
Su et al.

(10) Patent No.: US 8,173,760 B2
(45) Date of Patent: May 8, 2012

(54) DENDRON, POLYURETHANE WITH SIDE-CHAIN REGULAR DENDRON, AND PRODUCING METHODS THEREOF

(75) Inventors: Wen-Chiung Su, Longtan Township, Taoyuan County (TW); Wei-Ho Ting, Tanzi Township, Taichung County (TW); Chun-Ming Yeh, Zhongli (TW); Chia-Cheng Chang, Yuanlin Township, Changhua County (TW); Sheng-Hong Dai, Taichung (TW); Ru-Jong Jeng, Taichung (TW)

(73) Assignee: Chung-Shan Institute of Science and Technology, Armaments Bureau, Ministry of National Defense, Taoyuan County (TW)

( * ) Notice: Subject to any disclaimer, the term of this patent is extended or adjusted under 35 U.S.C. 154(b) by 131 days.

(21) Appl. No.: 12/714,515

(22) Filed: Feb. 28, 2010

(65) Prior Publication Data
US 2011/0213114 A1    Sep. 1, 2011

(51) Int. Cl.
*C08G 18/00* (2006.01)
(52) U.S. Cl. ............... 528/85; 528/53; 528/59; 528/65; 528/78; 528/82
(58) Field of Classification Search .............. 528/49, 528/60, 65, 53, 59, 78, 85, 82
See application file for complete search history.

(56) References Cited

U.S. PATENT DOCUMENTS

2005/0107563 A1*  5/2005  Hu et al. ............ 528/44
2009/0048418 A1*  2/2009  Su et al. ............ 528/53

OTHER PUBLICATIONS

Novel Side-Chain Dendritic Polyurethanes Based on Hydrogen Bonding Rich Polyurea/Malonamide Dendrons. Shenghong A. Dai. et al. Macromolecular Materials and Engineering. 2006, 291, 395-404.*
Polyurethane Elastomers through multi-hydrogen-bonded association of dendritic structures. Chen et al. Polymer 46 (2005) 11849-11857.*

* cited by examiner

*Primary Examiner* — Milton I Cano
*Assistant Examiner* — Michael L Leonard

(57) ABSTRACT

Methods for producing dendrons of different generations with hydrophobic functional end-groups, and for producing polyurethanes with the side-chain dendrons are disclosed step-by-step. The dendron with hydrophobic functional end-groups in the polyurethane systems, and the honeycomb-like structure thin films are obtained by a breath-figure process. The structures of dendrons and dendritic side-chain polyurethanes are respectively expressed in the following and the end-groups (R) of the dendron are long alkyl chains or perfluoroalkyl derivatives.

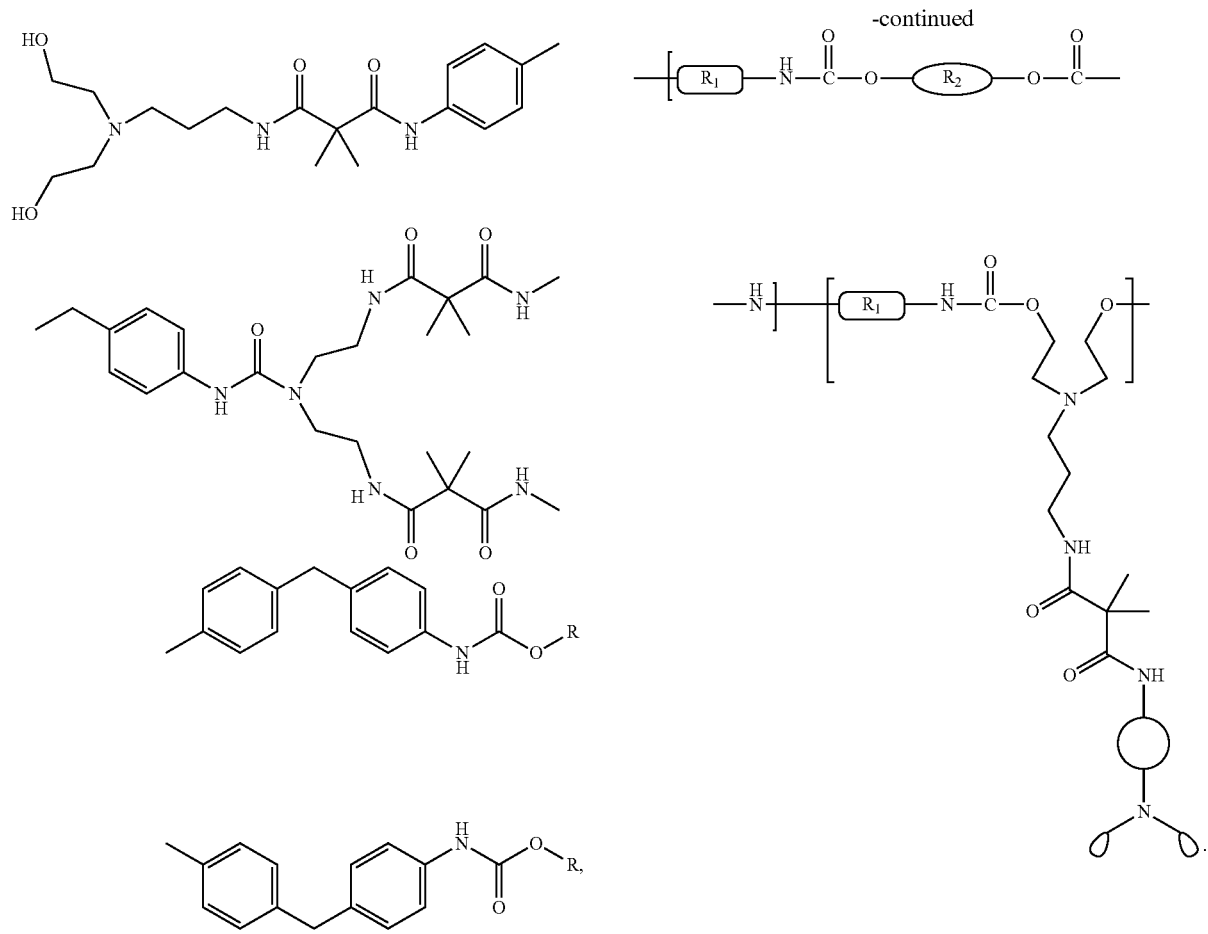
1 Claim, 8 Drawing Sheets

DENDRON, POLYURETHANE WITH SIDE-CHAIN REGULAR DENDRON, AND PRODUCING METHODS THEREOF

BACKGROUND OF THE INVENTION

1. Field of the Invention

This invention relates to a dendron with hydrophobic functional of end group, a polyurethane with the dendron, and producing methods thereof, and more particularly, the end group of the dendron includes alkyl chains or perfluoroalkyl chains, such as $C_{10}$~$C_{18}$ or perfluoroalkylethyl derivatives with more-than-four carbons.

2. Description of the Prior Art

In the recent years, there are more than 2000 relevant literatures about dendritic molecular chemistry. Dendrimer has a highly regular branched structure. By the step reaction, the molecular size thereof could be precisely controlled and it could be diversified. Buhleier et al. used addition and reduction reaction of acrylonitrile to produce dendrimer-like branched amines, i.e. hyperbranched polymer, in 1978. Tomalia et al. first published nano-dendritic poly(amidoamine) dendrimer in 1984 and also have established the record of earliest commercialization. The dendrimer consists of three basic structures including (1) core, (2) repeating unit, and (3) periphery group. The synthesis path could be classified by the growth direction into divergent type and convergent type.

In the prior art, for skipping the complicated steps of protection and dis-protection, improving productivity, and efficiently extending the generation growth, bifunctional build unit IDD (4-isocyanato-4'(3,3-dimethyl-2,4-dioxo-azetidino)diphenylmethane) is taken as the base. A series of regular dendrimers of derivatives of malonamide and urethane are developed by using the high reactivity of isocyanate and selective reactivity of azetidine-2,4-dione to perform alternating synthesis reaction with different alcohols and amines. The flow chart is shown in FIG. 1.

In addition, the side-chain dendrimer could be regarded as a structure copolymer of linear polymer and dendrimer. In the patent by Tomalia et al. in 1987, a dendrimer with a main chain of line polyethylenimine (PEI) is first mentioned. According to the literature, the side-chain dendrimer could be applied in the fields of self-assembly, nano leads of monomolecule, light-emitting material, catalyst, and so on.

SUMMARY OF THE INVENTION

The invention leads a long segment of alkyl chain and perfluoroalkyl chain in a dendritic structure. There is the effect of Van der Waal force between the molecules. In addition, the long alkyl chain or the perfluoroalkyl chain are constrained and bound together using the structure of dendron to form a sausage-like dendron, the structure of which is hydrophobic. On the other hand, the dendron has a urea/malonamide structure with strong hydrogen bond in the interior. Besides, the hydrogen bond interaction and the Van der Waal force in the respective interior and exterior of the dendron increase as the generation of the dendron increases.

After decyclization and addition reaction, the invention produces dendrons of different generations into a polyurethane system, so as to form a series of polyurethanes with side-chain regular dendron. Because of the hydrogen bond and the Van der Waal force in the respective interior and exterior of the dendron, the polyurethane with side-chain regular dendron could be produced with porosity using the breath figure method. Further, for increasing the practicability of the material, the invention controls the assembly of flexible and hard chain segments of the polyurethane with side-chain regular dendron so as to enhance the mechanical property of the porous film.

A scope of the invention is to lead dendron into a side chain of polyurethane, including a structure expressed by the following formula:

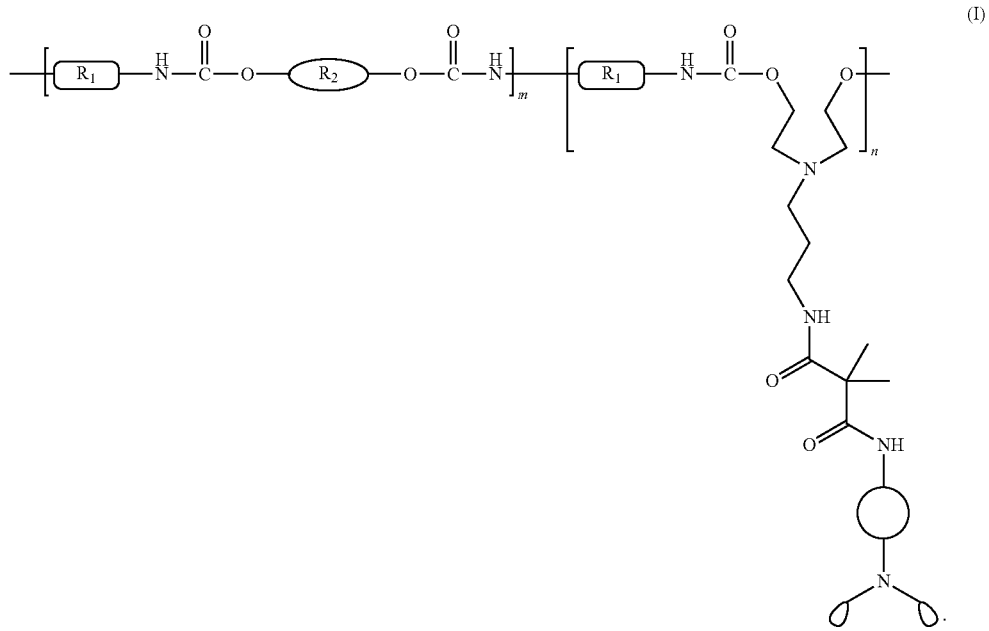

(I)

Therein, $R_1$ represents diisocyanate, and $R_2$ represents polyol.

The diisocyanate could be methylene di-p-phenyl diisocyanate (MDI), 1,6-hexamethylene diisocyanate (HDI), or isophorone diisocyanate (IPDI). The polyol could be polypropyl glycol (PPG), polycaprolactone (PCL), and polytetramethylene ether glycol (PTMEG).

According to an embodiment, when $R_1$ is MDI and $R_2$ is PPG, the compound for the formula (I) could be expressed by the following formula:
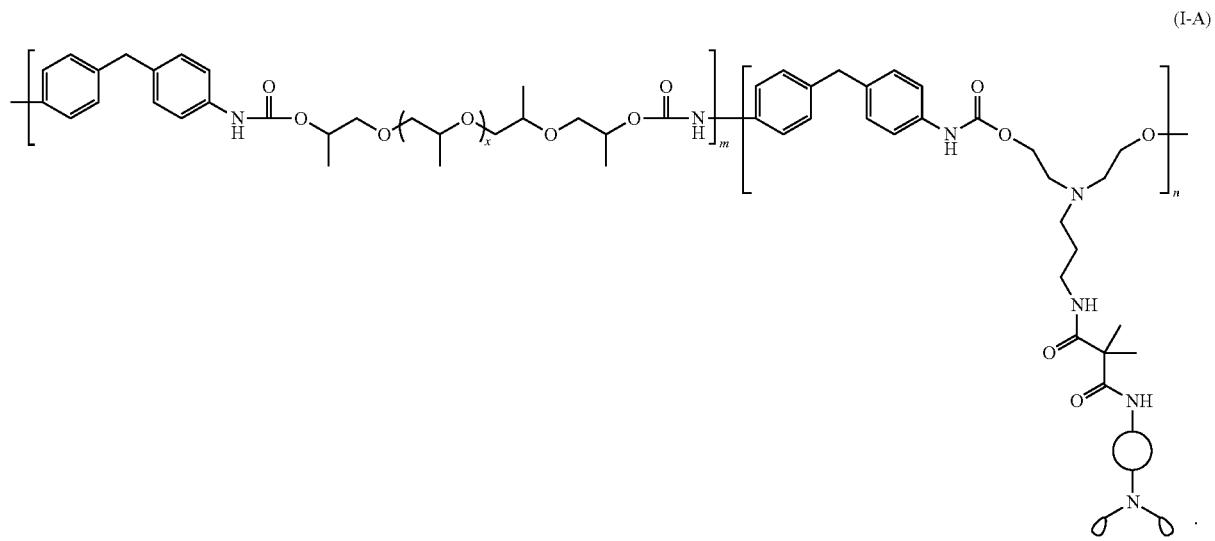
(I-A)
According to another embodiment, when $R_1$ is HDI and $R_2$ is PPG, the compound for the formula (I) could be expressed by the following formula:
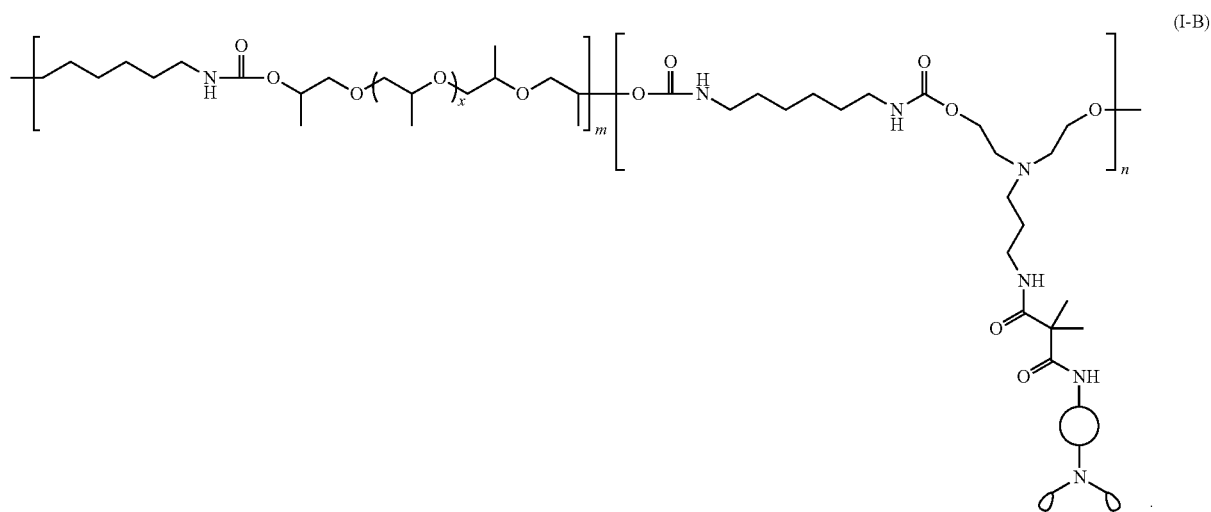
(I-B)

According to another embodiment, when $R_1$ is IPDI and $R_2$ is PPG, the compound for the formula (I) could be expressed by the following formula:
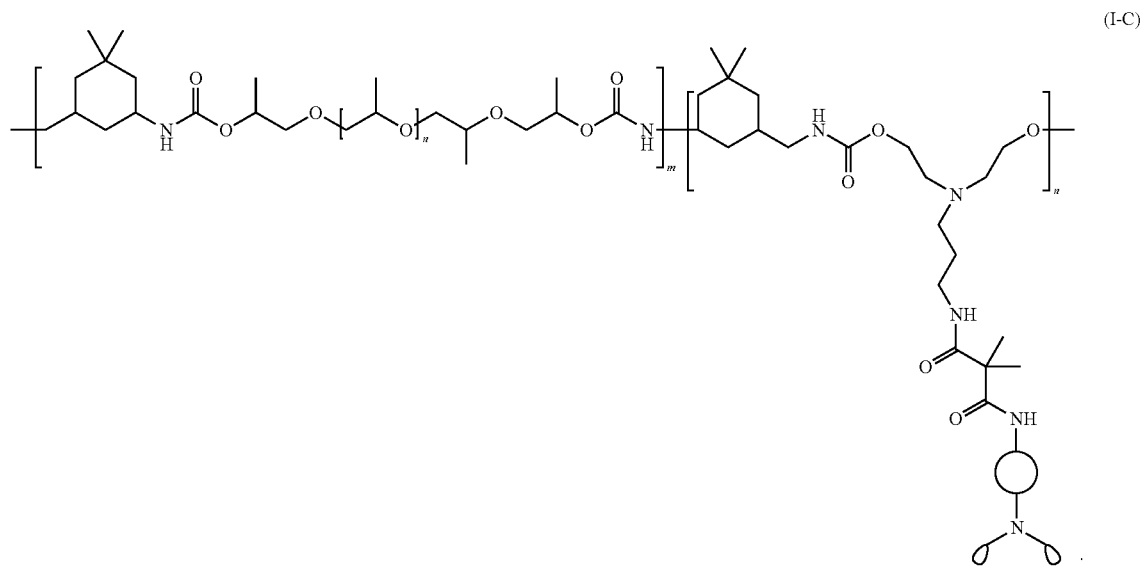
(I-C)
According to another embodiment, when $R_1$ is MDI and $R_2$ is PCL, the compound for the formula (I) could be expressed by the following formula:
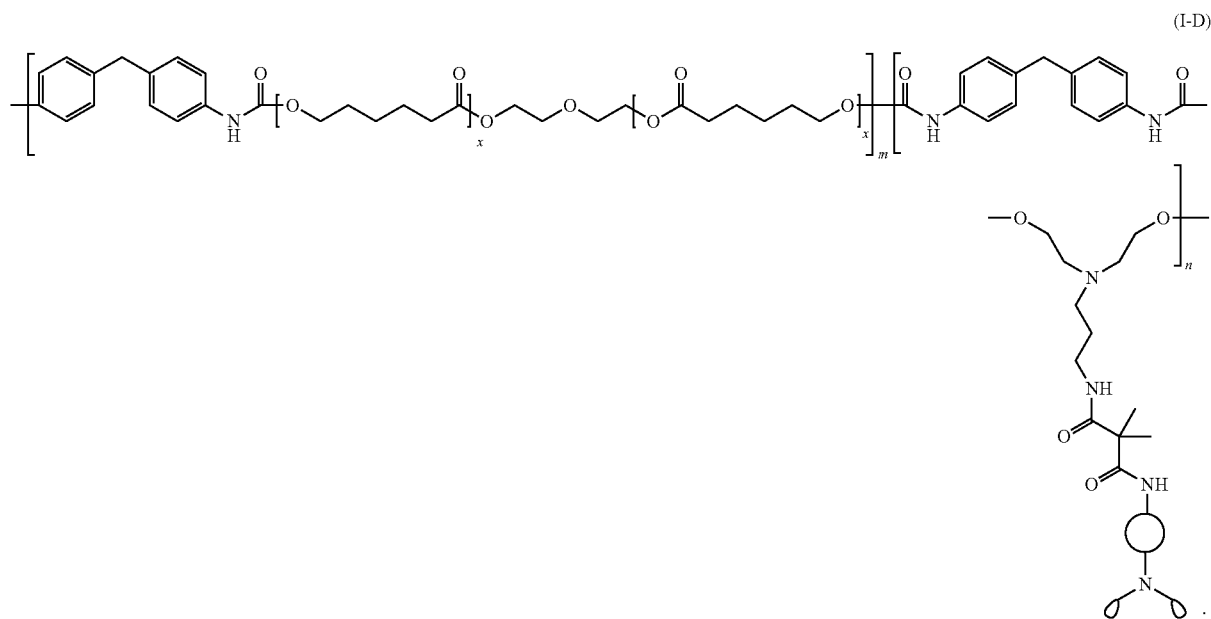
(I-D)

According to another embodiment, when $R_1$ is MDI and $R_2$ is PTMEG, the compound for the formula (I) could be expressed by the following formula:

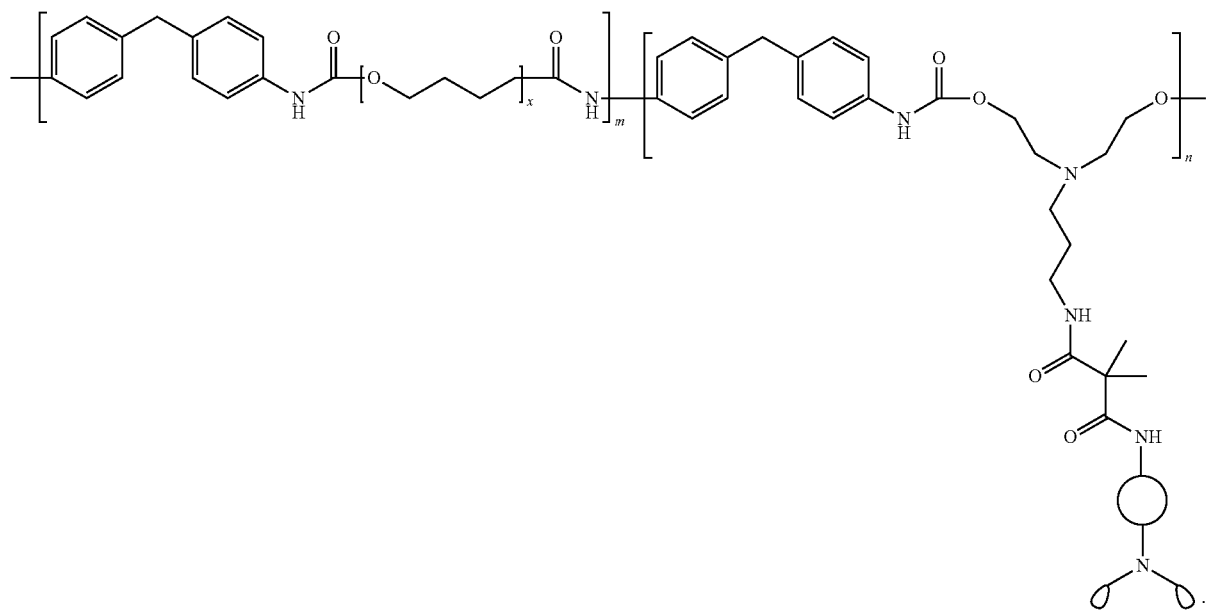

(I-E)

Films with honeycomb porosity are made of the above film material by the breath figure method. Because of the increase of roughness, the films can be hydrophobic, even superhydrophobic.

The advantage and spirit of the invention may be understood by the following recitations together with the appended drawings.

BRIEF DESCRIPTION OF THE APPENDED DRAWINGS

DETAILED DESCRIPTION OF THE INVENTION

According to an embodiment, a dendron is led to a side chain of the polyurethane of the invention, expressed by the following formula:

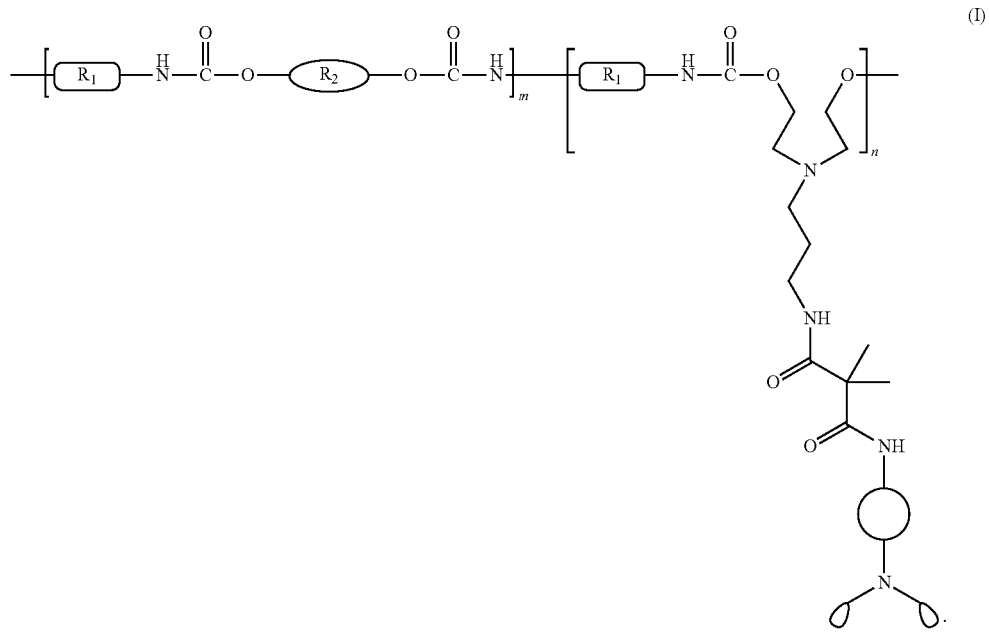

(I)

Therein, $R_1$ represents diisocyanate, and $R_2$ represents polyol.

The diisocyanate could be methylene di-p-phenyl diisocyanate (MDI), 1,6-hexamethylene diisocyanate (HDI), or isophorone diisocyanate (IPDI). The polyol could be polypropyl glycol (PPG), polycaprolactone (PCL), and polytetramethylene ether glycol (PTMEG).

Figure 1:
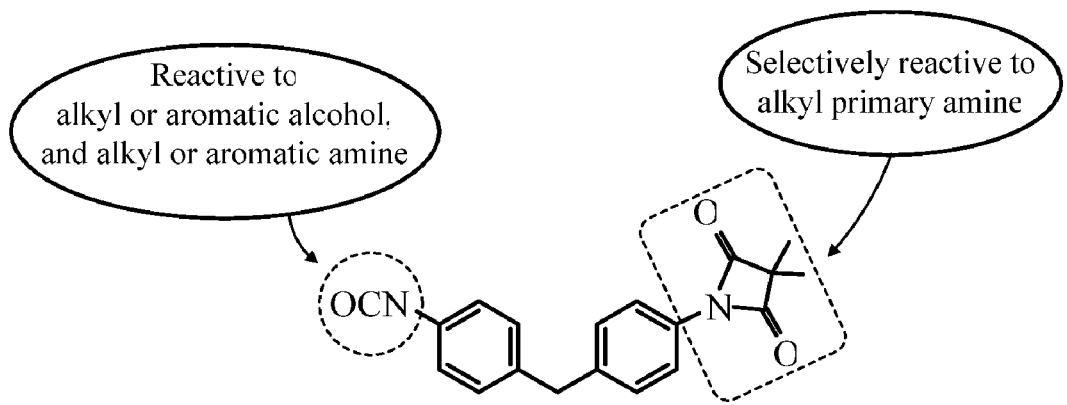
FIG. 1 is a schematic diagram illustrating the flow chart of the regular dendrimers in the prior art.
Figure 2:
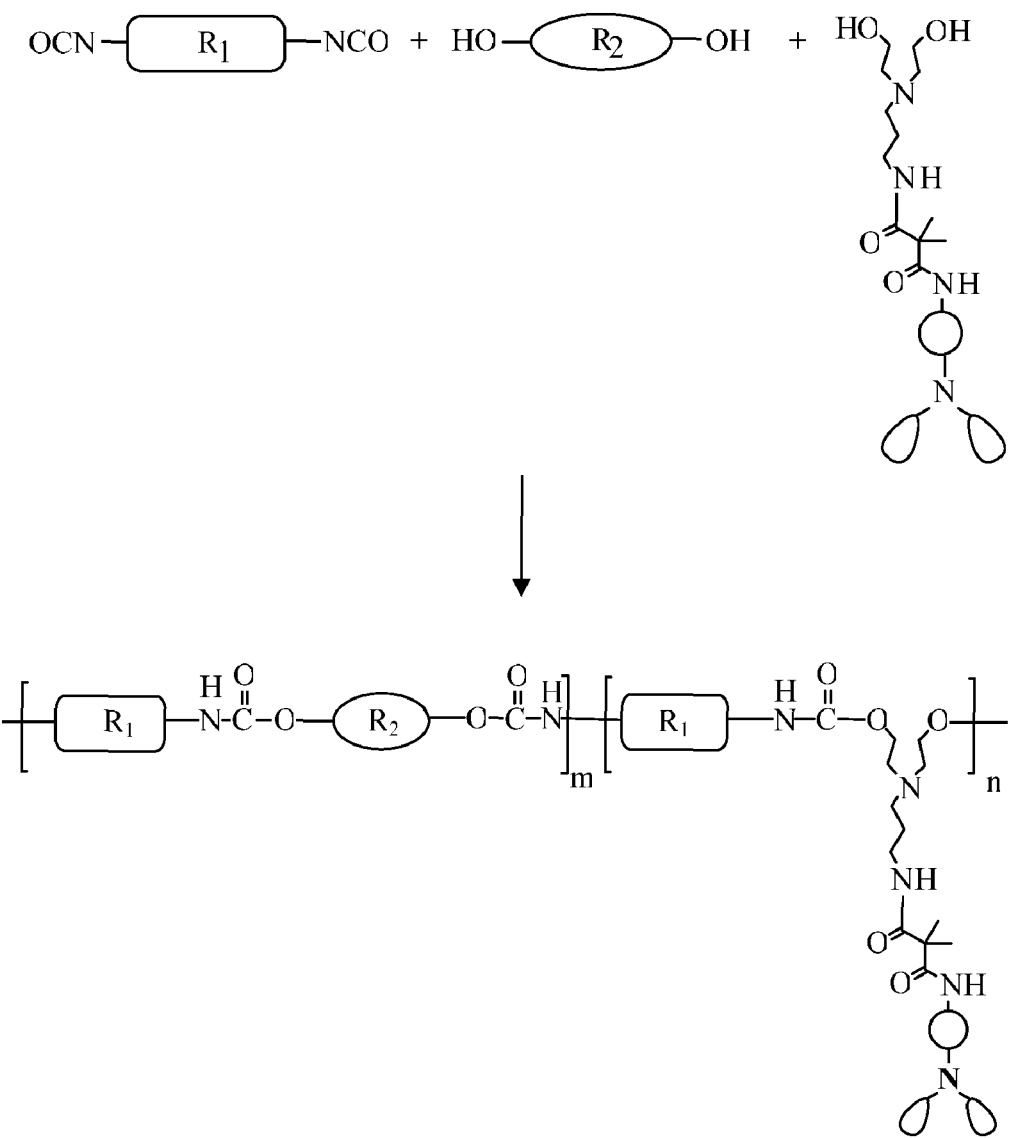
FIG. 2 is a flow chart of the process of leading the dendron into the side chain of the polyurethane.

The process of leading the dendron into the side chain of the polyurethane could be illustrated by the flow chart of FIG. 2. The process is described in detail by the following embodiments.

Embodiment I

The Synthesis of Dendron

Figure 3:
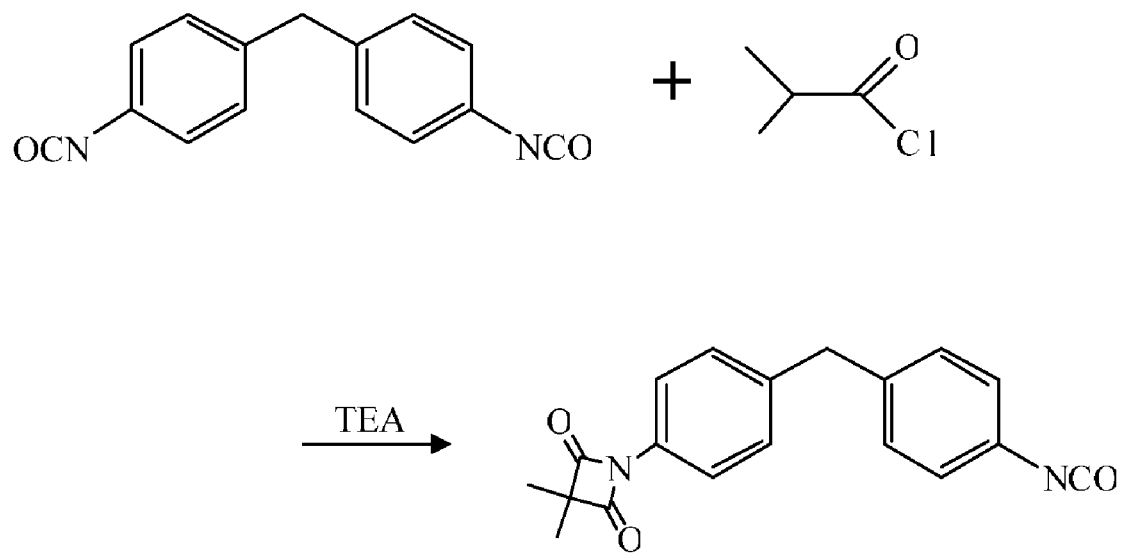
FIG. 3 is a flow chart of the reaction process of the unit IDD with selectivity.

In the embodiment, the reaction process of the unit IDD with selectivity is illustrated by the flow chart of FIG. 3.

Figure 4:
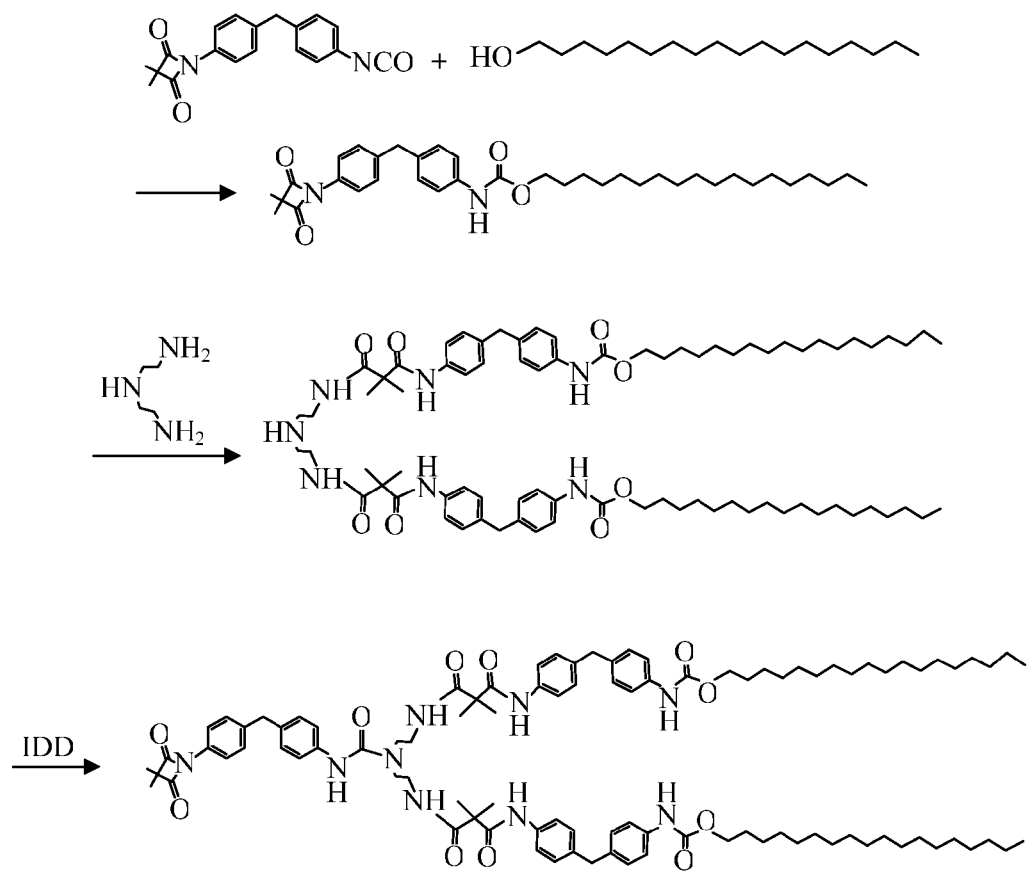
FIG. 4 is a flow chart of the reaction process of dendrons of different generations.

The IDD is used to react with stearyl alcohol. Then, primary amine is used to perform decyclization reaction on azetidine-2,4-dione. By the step-by-step synthesis steps, dendrons of different generations are synthesized. The reaction process is illustrated by the flow chart of FIG. 4.

The above dendron could be made by the following steps. First, bifunctional build unit IDD is dissolved in tetrahydrofuran (THF) to form a first solution. Alcohol is added into the first solution at 70 degrees in Celsius with aerating nitrogen of gas for 4 hours. After the reaction ends, the first solution is dropped into methanol for precipitation and stirred at 70 degrees in Celsius for 6 hours. A first product is collected from the solution by exhaust filtering. The first product is then dried to obtain a first intermediate (G-0.5).

Next, the first intermediate (G-0.5) is disposed a reaction flask to be dissolved in dehydrated tetrahydrofuran to form a second solution. Nitrogen of gas is aerated in the second solution. The second solution is stirred and slowly added with diethylenetriamine (DETA) at 70 degrees in Celsius. The second solution is kept in reaction for 3 hours after a second product starts being precipitated. Afterwards, the second solution is cooled to the room temperature, washed with tetrahydrofuran, and dried by exhaust filtering so as to obtain a dendrimer (G-1).

Then, the dendrimer (G-1) is mixed with dehydrated tetrahydrofuran to form a third solution. The third solution is stirred with aerating nitrogen of gas at 75 degrees in Celsius. After the dendrimer (G-1) has been dissolved, the bifunctional build unit IDD is added in the third solution for reaction for 4 hours. A part of the tetrahydrofuran is drawn. The third solution is dropped into methanol for precipitation; a second intermediate (G-1.5) is obtained by exhaust filtering and then drying.

Afterwards, the above steps are repeated for producing a third intermediate (G-2.5) and a fourth intermediate (G-3.5). At last, the first intermediate (G-0.5), the second intermediate (G-1.5), the third intermediate (G-2.5), and the fourth intermediate (G-3.5) are dissolved into dehydrated tetrahydrofuran and mixed with N-(3-aminopropyl)diethanolamine (APDEA) so as to form a fourth solution. The fourth solution is kept in reaction under aerating nitrogen of gas at 75 degrees in Celsius for 48 hours. After the intermediate (G-1.5) have completely reacted, the fourth solution is dropped into methanol for precipitation and washing incompletely-reacted APDEA out. After the solution has been stirred for 6 hours, the dendron is then obtained by exhaust filtering and then drying.

For leading the dendron into the system of the polyurethane, a chemical modification is required. In the embodiment, primary amine and azetidine-2,4-dione are used to perform decyclization reaction to synthesize the intermediate (G-1.5)-glycol with functional group of glycol, so as to be used as chain extender in the polyurethane system. The above process is illustrated in the flow chart of FIG. 5.

Figure 6:
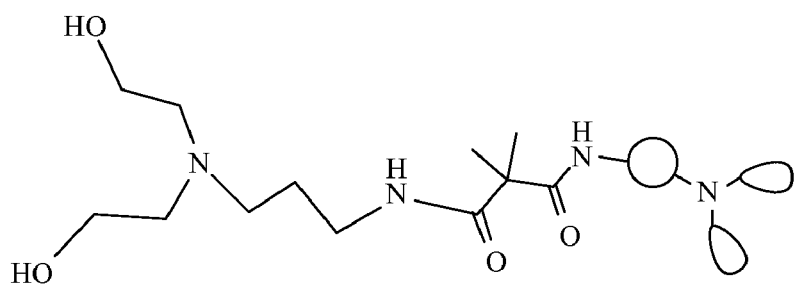
FIG. 6 is a schematic diagram of the dendron.

Similar to the synthesis of dendron of alkyl chain, derivative relative to perfluoroalkylethyl ethyl alcohol is led to make the end of the dendron with perfluorooctyl ethyl group. The dendron has low surface energy, so films made of the dendron can be superhydrophobic. The dendron is schematically illustrated in FIG. 6.

Embodiment II

The Synthesis of the Compound (I-A)

Preparing raw materials of MDI and PPG depends on the ratio of flexible and hard chain segments. MDI is heated at 50 degrees in Celsius to melt; the clear portion of the upper liquid is taken. PPG is dehydrated in vacuum in an oven, then heated to 80 degrees in Celsius, and exhausted for 6 hours. Next, MDI and PPG are dissolved in dimethyl formamide (DMF) with aerating nitrogen of gas at 60 degrees in Celsius for half an hour for reaction. Then, the dendritic compound (G-1.5)-glycol is added in the solution. Dibutyltin dilaurate is taken as catalyst. The solution is heated up to 80 degrees in Celsius for 3.5 hours for reaction. After the reaction ends, the solution is poured onto a disk of Teflon to be disposed in an oven for removing solvent and forming films.

Embodiment III

The Synthesis of the Compound (I-B)

Preparing raw materials of HDI and PPG depends on the ratio of flexible and hard chain segments. HDI is used without purification. PPG is dehydrated in vacuum in an oven, then heated to 80 degrees in Celsius, and exhausted for 6 hours. Next, HDI and PPG are dissolved in DMF with aerating nitrogen of gas at 60 degrees in Celsius for half an hour for reaction. Then, the dendritic compound (G-1.5)-glycol is added in the solution. Dibutyltin dilaurate is taken as catalyst. The solution is heated up to 80 degrees in Celsius for 3.5 hours for reaction. After the reaction ends, the solution is poured onto a disk of Teflon to be disposed in an oven for removing solvent and forming films.

Embodiment IV

The Synthesis of the Compound (I-C)

Preparing raw materials of IPDI and PPG depends on the ratio of flexible and hard chain segments. IPDI is used without purification. PPG is dehydrated in vacuum in an oven, then heated to 80 degrees in Celsius, and exhausted for 6 hours. Next, IPDI and PPG are dissolved in DMF with aerating nitrogen of gas at 60 degrees in Celsius for half an hour for reaction. Then, the dendritic compound (G-1.5)-glycol is added in the solution. Dibutyltin dilaurate is taken as catalyst. The solution is heated up to 80 degrees in Celsius for 3.5 hours for reaction. After the reaction ends, the solution is poured onto a disk of Teflon to be disposed in an oven for removing solvent and forming films.

Embodiment V

The Synthesis of the Compound (I-D)

Preparing raw materials of MDI and PCL depends on the ratio of flexible and hard chain segments. MDI is heated at 50 degrees in Celsius to melt; the clear portion of the upper liquid is taken. PCL is dehydrated in vacuum in an oven, then heated to 80 degrees in Celsius, and exhausted for 6 hours. Next, MDI and PCL are dissolved in DMF with aerating nitrogen of gas at 60 degrees in Celsius for half an hour for reaction. Then, the dendritic compound (G-1.5)-glycol is added in the solution. Dibutyltin dilaurate is taken as catalyst. The solution is heated up to 80 degrees in Celsius for 3.5 hours for reaction. After the reaction ends, the solution is poured onto a disk of Teflon to be disposed in an oven for removing solvent and forming films.

Embodiment V

The Synthesis of the Compound (I-E)

Preparing raw materials of MDI and PTMEG depends on the ratio of flexible and hard chain segments. MDI is heated at 50 degrees in Celsius to melt; the clear portion of the upper liquid is taken. PTMEG is dehydrated in vacuum in an oven, then heated to 80 degrees in Celsius, and exhausted for 6 hours. Next, MDI and PTMEG are dissolved in DMF with aerating nitrogen of gas at 60 degrees in Celsius for half an hour for reaction. Then, the dendritic compound (G-1.5)-glycol is added in the solution. Dibutyltin dilaurate is taken as catalyst. The solution is heated up to 80 degrees in Celsius for 3.5 hours for reaction. After the reaction ends, the solution is poured onto a disk of Teflon to be disposed in an oven for removing solvent and forming films.

Figure 5:
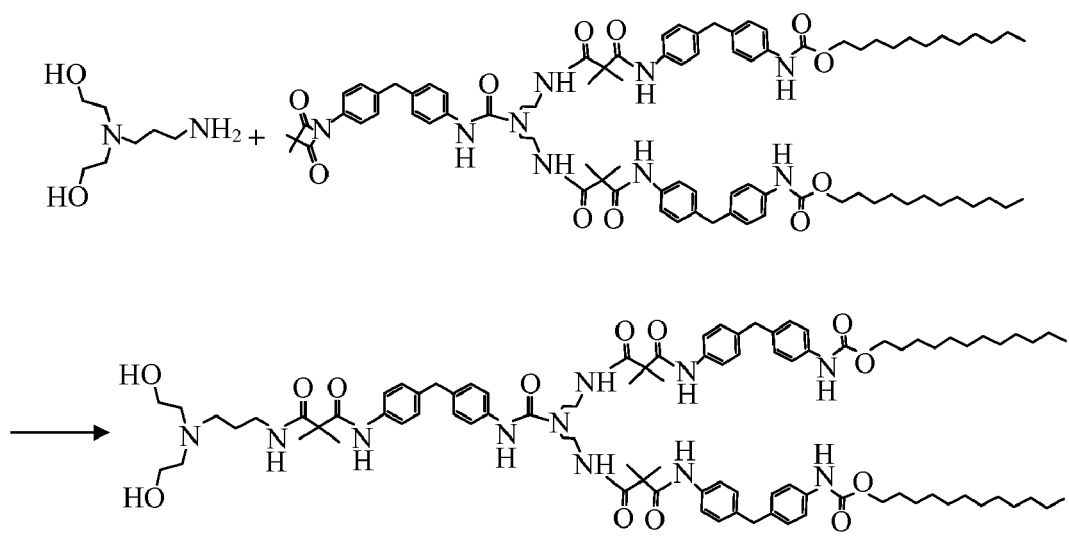
FIG. 5 is a flow chart of the reaction process of the dendritic chain extender to be used in the polyurethane system.
Figure 7:
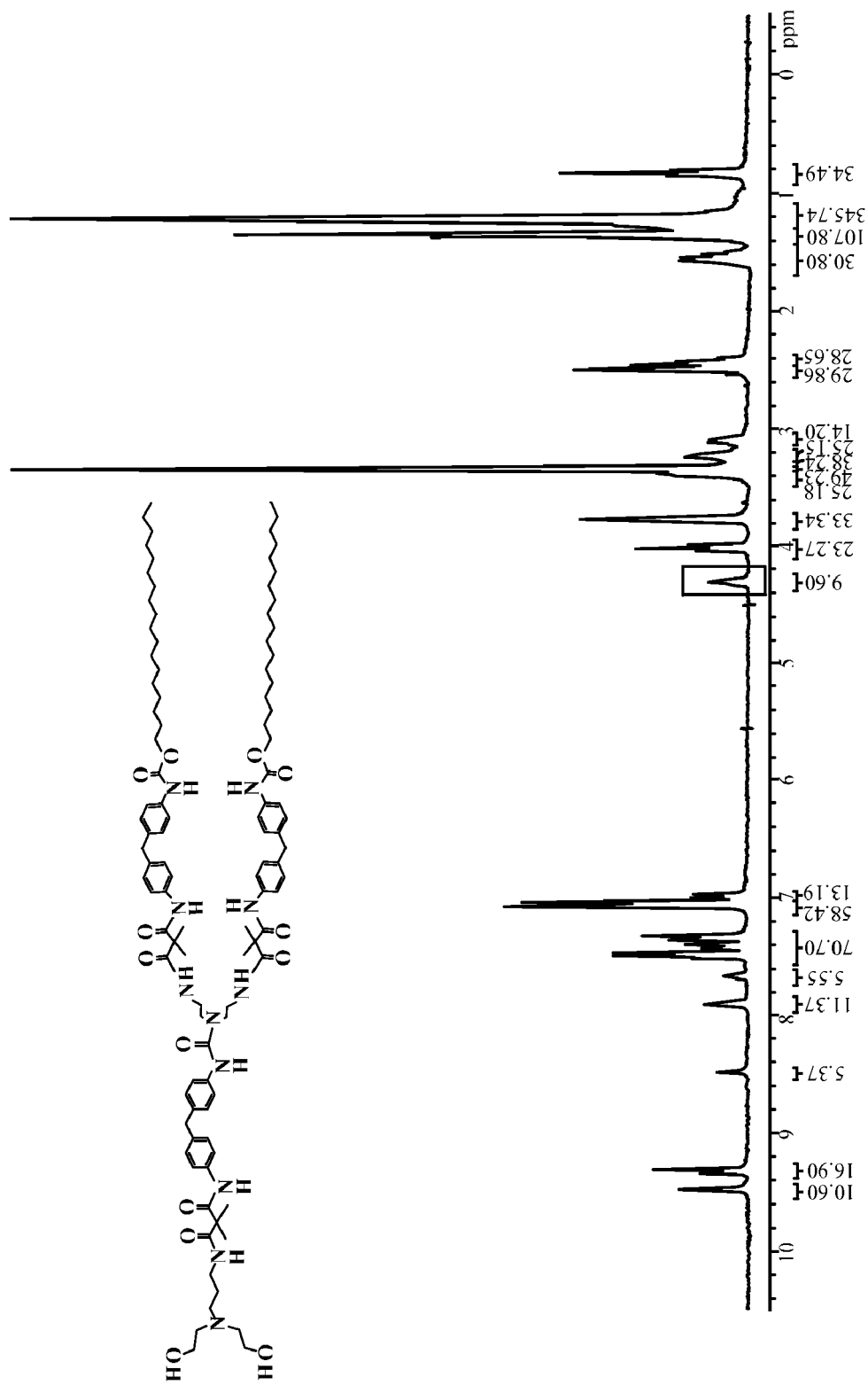
FIG. 7 is a $^1H$ NMR spectrogram of the dendritic chain extender in FIG. 5.
Figure 8:
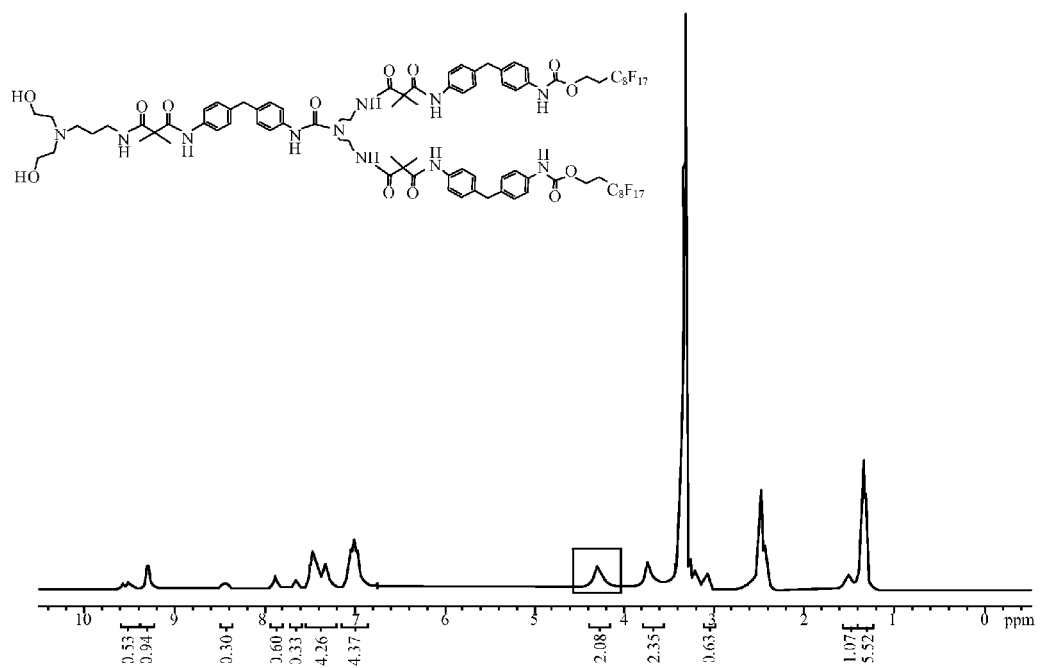
FIG. 8 is a $^1H$ NMR spectrogram of the dendritic chain extender with $C_8F_{17}$.
Figure 9:
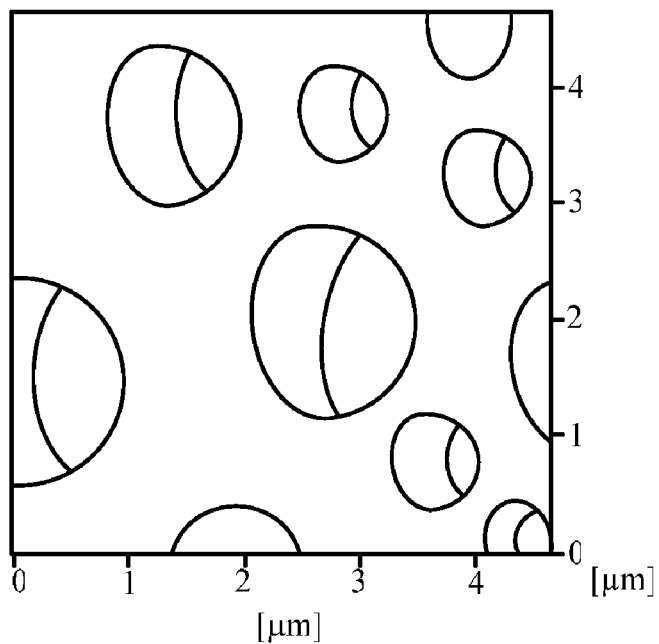
FIG. 9 is an AFM diagram of a film made of the polyurethane with MDI and PPG.
Figure 10:
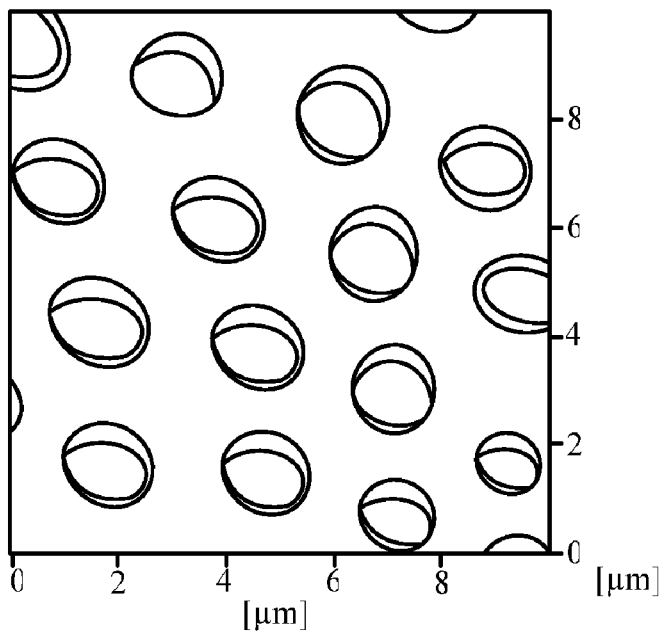
FIG. 10 is an AFM diagram of a film made of the polyurethane with HDI and PPG.

In addition, the $^1$H NMR spectrogram of the chain extender in FIG. 5 is illustrated in FIG. 7; the $^1$H NMR spectrogram of the chain extender with $C_8F_{17}$ is illustrated in FIG. 8. A film made of the polyurethane with MDI and PPG or with HDI and PPG is porous, shown in FIGS. 9 and 10.

With the example and explanations above, the features and spirits of the invention will be hopefully well described. Those skilled in the art will readily observe that numerous modifications and alterations of the device may be made while retaining the features and spirit of the invention. Accordingly, the above disclosure should be construed as limited only by the metes and bounds of the appended claims.

What is claimed is:

1. A process for producing a polyurethane with a side-chain regular dendron, formed in a two-stage reaction,
   wherein the side-chain regular dendron is formed in a three-stage reaction including the following five steps:
   (i) stage 1 reaction:
   forming a first solution by dissolving bifunctional build unit IDD in tetrahydrofuran, adding alcohol into the first solution at 70° C. with aerating nitrogen of gas for 4 hours, dropping the first solution into a methanol for precipitation and stirring at 70° C. for 6 hours, and obtaining a first intermediate by collecting a first product with exhaust filtering and drying;
   (ii) stage 2 reaction:
   forming a second solution by dissolving the first intermediate in dehydrated tetrahydrofuran,
   aerating nitrogen of gas,
   stirring the second solution and slowly adding diethylenetriamine at 70° C., keeping in reaction for 3 hours after a second product starts being precipitated,
   cooling the second solution to room temperature,
   washing the second product with mass tetrahydrofuran,
   obtaining a dendrimer by drying the second product with exhaust filtering;

(iii) stage 3 reaction:
forming a third solution by mixing the dendrimer with dehydrated tetrahydrofuran, stirring the third solution with aerating nitrogen of gas at 75° C.,
after dissolving the dendrimer, adding the bifunctional build unit IDD in the third solution for reaction for 4 hours,
drawing part of the tetrahydrofuran,
dropping the third solution into methanol for precipitation,
obtaining a second intermediate by exhaust filtering and drying;
(iv) repeating the above steps to form a third intermediate and a fourth intermediate; and
(v) forming a fourth solution by dissolving the second intermediate, the third intermediate, and the fourth intermediate into dehydrated tetrahydrofuran and mixing with APDEA,
keeping the fourth solution in reaction under aerating nitrogen of gas at 75° C. for 48 hours,
after the intermediates are completely reacted, precipitating the fourth solution with methanol and washing incompletely-reacted APDEA out, and
obtaining the dendron by exhaust filtering and drying after stirring for 6 hours; and
the two-stage reaction, by which the polyurethane is formed, includes:

(I) a first stage reaction:
forming a reaction system by disposing purified R1 and dehydrated R2 in a flask at 60° C. with aerating nitrogen of gas, keeping the reaction system in circumference reaction for half an hour,
wherein R1 is one selected from an R1 group containing methylene di-p-phenyl diisocyanate (MDI), 1,6-hexamethylene diisocyanate (HDI), and isophorone diisocyanate (IPDI),
R2 is one selected from an R2 group containing polypropyl glycol (PPG), polycaprolactone (PCL), and polytetramethylene ether glycol (PTMEG), and
R1 is MDI, when R2 is PPG,
R1 is IPDI, when R2 is PPG,
R1 is MDI, when R2 is PCL, and
R1 is MDI, when R2 is PTMEG, with the first stage reaction followed by a second stage reaction;
(II) a second stage reaction:
adding into the reaction system, the dendron, as a chain extender, and dibutyltin dilaurate, as a catalyst,
heating the reaction system to 80° C. and in reaction for three-and-half hours, and pouring a solution in the reaction system onto a disk of Teflon disposed in an oven for removing solvent.

* * * * *